United States Patent [19]

Kirby et al.

[11] Patent Number: 4,490,469

[45] Date of Patent: Dec. 25, 1984

[54] PRODUCTION OF ETHANOL BY FERMENTATION

[75] Inventors: Kevin D. Kirby, Lower Plenty; Christopher J. Mardon, Elsternwick, both of Australia

[73] Assignee: Commonwealth Scientific and Industrial Research Organization, Campbell, Australia

[21] Appl. No.: 229,360

[22] Filed: Jan. 29, 1981

[30] Foreign Application Priority Data

Jan. 30, 1980 [AU] Australia .................... PE2181/80
Apr. 2, 1980 [AU] Australia .................... PE3006/80

[51] Int. Cl.$^3$ .................................... C12P 7/06
[52] U.S. Cl. .................................... 435/161
[58] Field of Search ............... 435/161, 163, 165, 162; 426/11, 16, 31

[56] References Cited

U.S. PATENT DOCUMENTS

| | | | |
|---|---|---|---|
| 1,709,610 | 4/1929 | Roza et al. | 435/163 |
| 3,093,548 | 6/1963 | Coates et al. | 435/162 |
| 3,835,222 | 9/1974 | Wisdom et al. | 426/49 |
| 3,968,254 | 7/1976 | Rhodes et al. | 426/18 |
| 4,055,666 | 10/1977 | Jeffreys et al. | 426/31 |
| 4,094,742 | 6/1978 | Bellamy | 435/163 X |
| 4,140,801 | 2/1979 | Hilton et al. | 426/49 |
| 4,242,455 | 12/1980 | Muller et al. | 435/165 X |
| 4,288,550 | 9/1981 | Ishida et al. | 435/161 X |

FOREIGN PATENT DOCUMENTS 2013716  8/1979  United Kingdom .

OTHER PUBLICATIONS

Rolz et al., "Ethanol from Sugar Cane: Ex Ferm Concept", Biotechnol. & Bioeng., vol. XXI, (1979), pp. 2347-2349.
Flickinger, "Current Biological Research in Conversion of Cellulosic Carbohydrates into Liquid Fuels", Biotechnol. & Bioeng., vol. XXII, (1980), pp. 27-48.
Rudolph et al., "Direct Production of Ethanol from Sugar Cane", Paper presented at International Sumposium on Alcohol Fuel Technology, Wolfsburg, DBR, (1977).
Adams, "Small Scale Vinegar Production from Bananas", Tropical Science, vol. 20, pp. 11-19, (1978).
Hesseltine, "Solid State Fermentation-Parts 1&2", Process Biochemistry, Jul.-Aug. 1977, pp. 24-27, Nov. 1977, pp. 29-32.
Ueda et al., "Alcoholic Fermentation of Raw Starch Without Cooking By Using Black-Koji Amylase", J. of Fermentation Technology, vol. 58, (1980), pp. 237-242.
Tarac Industries, "Tarac 1930-1980", Investigator Press, Hawthorndene So. Australia, 1980, pp. 41-52.

*Primary Examiner*—R. B. Penland
*Attorney, Agent, or Firm*—Cushman, Darby & Cushman

[57] ABSTRACT

The production of ethanol, particularly ethanol used as a fuel, optionally in conjunction with gasoline (petrol) may be produced from carbohydrate containing material, such as starch-containing material or sugar-containing material, by a solid phase fermentation process.

19 Claims, 1 Drawing Figure

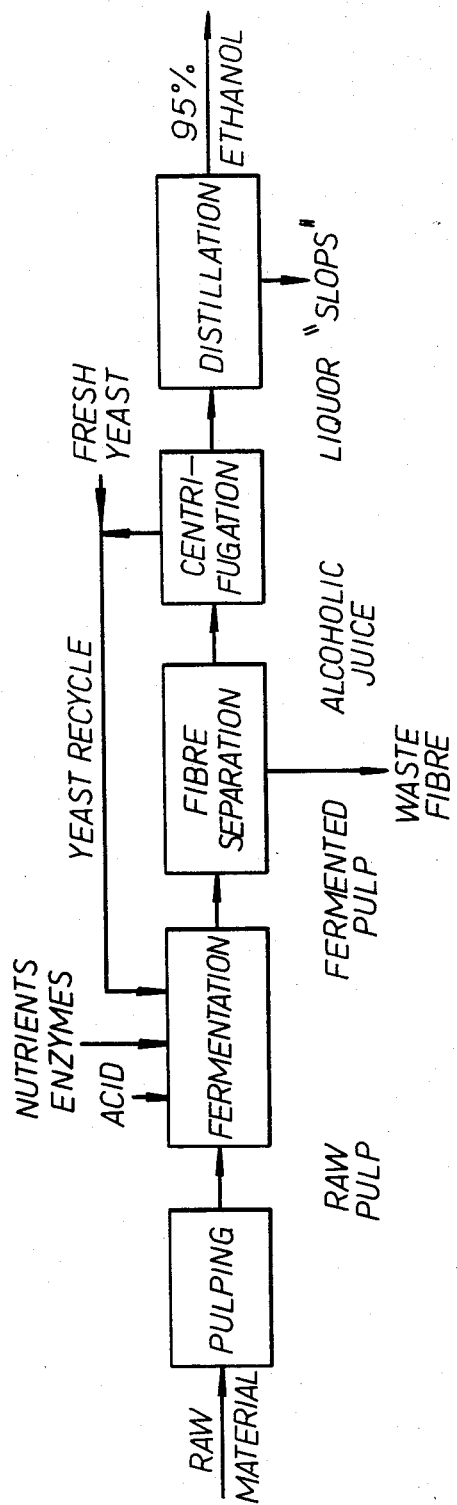

PRODUCTION OF ETHANOL BY FERMENTATION

This invention relates to the production of ethanol particularly ethanol for use as a fuel, by fermentation of a sugar-containing material or of a starch-containing material, or of a material containing both substances. In particular, it relates to the production of fuel ethanol in high yields by a process which is economical on a much smaller scale than is the case with existing technology and which requires only the use of simple and relatively inexpensive equipment.

Attention has recently been focused on the use of ethanol, particularly when blended with petrol (or "gasoline"), as a fuel for internal combustion engines of motor vehicles. The conversion of sugar into ethanol by yeast fermentation is well known, and many sugar-containing materials have been investigated for use in this method of production of ethanol. In general, these processes are based on the initial production of a sugar-containing liquid, followed by liquid-phase yeast fermentation thereof.

Sugar beets are a well-known and widely-used source of sugars, particularly sucrose, and in one known process for the extraction of sugar therefrom, the beets are sliced into long thin strips or "cossettes" prior to extraction of sugar therefrom by a diffusion process. The cossettes are then fed to a continuous sloped diffuser through which they are carried upwardly from the lower end. Hot water is fed to the diffuser at the upper end, flowing down counter-current to the direction of cossette movement and leaving the lower end of the diffuser as a sugar-containing liquid.

As far as ethanol production from starch containing materials is concerned, the normal method starting with starch crops is to mill and cook the starchy material to gelatinise the starch, to liquefy and hydrolyse the starch to sugars with malt, fungi or enzymes, and then to ferment the sugars to alcohol by means of liquid-phase yeast fermentation.

It is an object of the present invention to provide an improved process whereby ethanol, particularly fuel ethanol, can be produced in high yield from a sugar-containing material, particularly, sugar beet, sugar-cane, fodder beet, mangolds, or the like, without the necessity of prior extraction of the sugar from the sugar containing material. It will be appreciated that if the necessity for prior extraction of the material can be avoided, the overall process of ethanol production will be simplified and made more economic.

It is a further object of the present invention to provide an improved process for producing ethanol, particularly fuel ethanol, from starch-containing crops such as vegetables and cereal grains, for example potatoes, cassava, wheat, barley, corn, triticale, grain sorghum, vegetable waste and the like without the necessity for prior cooking of the starch-containing material or for separately converting starch into sugar prior to the fermentation of the sugar, or for the prior extraction of the sugar produced by the starch.

According to the present invention there is provided a process for the production of ethanol by fermentation of a carbohydrate-containing material, comprising (a) crushing or pulping said carbohydrate-containing material to produce a pulp containing substantially no free liquid and comprising particles of said material having diameters of the range up to about 10 mm;

(b) where necessary saccharifying and, if desired, heating said pulp to convert non-sugar carbohydrates in said material to sugars;

(c) mixing a suspension of yeast with said pulp (simultaneously with or subsequent to said saccharification, if used) and maintaining said mixture under fermentation conditions to allow said yeast to convert sugars in said pulp to ethanol; and (d) extracting ethanol from said fermented pulp.

According to a first aspect of the present invention there is provided a process for the production of ethanol by fermentation of a sugar-containing material which comprises:

(a) crushing or pulping said sugar containing material to produce a pulp containing substantially no free liquid and comprising particles of said material having diameters of the range up to about 10 mm;

(b) mixing a suspension of yeast with said pulp;

(c) maintaining said mixture under fermentation conditions to allow said yeast to convert sugar in said particles to ethanol; and (d) extracting ethanol from said fermented pulp.

According to the second aspect of the present invention, there is provided a process for the production of ethanol by fermentation of a starch-containing material, which comprises:

(a) crushing or pulping said starch-containing material to produce a pulp containing substantially no free liquid and comprising particles of said material having diameters of the range up to about 10 mm;

(b) saccharifying and, if desired, heating said pulp to convert starch in said material to sugars;

(c) simultaneously with or subsequent to said saccharification, mixing a suspension of yeast with said pulp and maintaining said mixture under fermentation conditions to allow said yeast to convert sugars in said pulp to ethanol; and (d) extracting ethanol from said fermented pulp.

Preferably, in both aspects of the present invention the ethanol is extracted from the fermented pulp by pressing or squeezing the pulp to express the ethanol-containing juice. The juice also contains most of the yeast from the fermented pulp, together with some fine fibres from the sugar-containing material or the starch-containing material. The yeast and fibres may be separated from the juice by known methods such as filtration or more preferably centrifugation, and, then may be recycled to the fermentation stage if desired. It is to be noted at this stage that the recycling of the fine fibres recovered with the yeast to the fermentation stage does not give rise to any problems since the fibre volume is small and should reach an equilibrium value in a fairly short time.

Essentially, the process of the second aspect of the present invention, directed towards the use of starch-containing starting material, comprises a further development of the process of the first aspect of the present invention directed to the use of sugar-containing material as the starting material, in that the further development comprises the additional process step of saccharifying or hydrolysing the starch in the starch-containing material to sugars prior to or simultaneously with fermentation. Saccharification or hydrolysis may be carried out by any known process, for example by acid hydrolysis, however, it is preferably carried out by enzymatic means, particularly by the addition of amylase. If desired, the rate of saccharification of the starch may be promoted by heating the pulp during this process step.

The saccharification or hydrolysis of starch to sugars by chemical or enzymatic means is, of course, well known and further description of this step at this stage is considered unnecessary. As noted above, the saccharification of the starch-containing material may be performed prior to the yeast fermentation of the sugars. However, the simultaneous saccharification and fermentation of the starch-containing material offers distinct advantages from the point of view of simplification of the process technology. In addition, such simultaneous performance of these steps may be advantageous in that the fermentation of sugars as they are produced may assist in the more complete saccharification of the starch.

It is an important aspect of the present invention that the sugar containing material or the starch-containing material or material containing both sugar and starch be crushed or pulped to produce small particles of up to about 10 mm. diameter, however the precise shape and thickness of the particles is not essential to this invention. Where the sugar-containing material is sugar beet or fodder beet, it is preferred that the particles be of diameter up to about 5 mm., however, the particle size can be varied as desired for other sugar-containing materials, and any suitable pulping or crushing equipment may be used in order to effect this pulping of the sugar-containing material.

Since the pulp contains little or no free liquid, it is generally, as a rule, relatively stiff in consistency and cannot flow of its own accord. Nevertheless, it has been found that in accordance with the present invention it can be added directly to a fermenter so as to effect a "solid phase" fermentation of the pulp. The term "solid phase" fermentation as used in the present specification is generally used to describe microbial attack, usually by fungi, on moist solid particles. The term is used for the process of the present invention since it involves fermentation of moist solid particles without the addition of further liquid (apart from the very small amount associated with the acid and yeast suspension). It has been found that baker's yeast was able to ferment the sugars in pulped sugar crops without the need for prior extraction of the sugar or agitation of the pulp. Moreover, the solid phase fermentation proceeded more rapidly than those in the liquid phase and the yield of ethanol was about the same.

Preferably, in order to achieve appropriate conditions for fermentation of the pulp, an acid such as sulphuric acid or an alkali may be added to the pulp to adjust the pH to a range of between about 4 and 6. Preferably, the pH is adjusted to about 4.5 in the case where sugar-containing starting material is used in the process of the invention. Prior sterilization of the raw pulp is not required.

As noted above, a suspension of yeast is added to the pulp and, by way of example, the suspension may contain up to 20% by weight of yeast, preferably about 10%. Preferably, 10 gm dry weight of yeast per kg of wet pulp is added to the pulp. Typically, in the production of fuel ethanol by this process, the yeast used is the strain *Saccharomyces cerevisiae* in the form of active dry baker's yeast or compressed yeast. It is to be noted that high alcohol tolerant strains of yeast or thermophilic strains of yeast may be used. The proportion of yeast suspension added to the pulp will depend upon the rate of fermentation required and can be adjusted as desired.

Growth nutrients for the yeast may also be added to the mixture, however it is found that in many instances such nutrients will not be necessary. In addition, enzymes such as pectinases or cellulases to hydrolyze pectin and cellulose, respectively, in the pulp may be added if desired. The yeast suspension is then well mixed with the pulp together with any other materials added to the fermenter and the mixture maintained under fermentation conditions. Preferably, these fermentation conditions include a temperature of about 25°–50° C. in order that the fermentation will proceed rapidly. Although water contained in the yeast suspension is added to the pulp, it is found that this is taken up by the pulp and does not remain in the mixture as free liquid.

On an industrial scale, mixing of the pulp and yeast suspension in the fermenter and heating of the mixture (or cooling as required) may be best achieved by circulating the pulp through an external heat exchanger with a suitable pump. Throughout the fermentation, the contents of the fermenter remain substantially solid and at no stage are able to flow on their own accord. Nevertheless, the particle size of the pulp is sufficiently small to make it readily pumpable.

On completion of the fermentation, the fermented pulp is treated to extract the ethanol therefrom. In one such method for extraction of the ethanol which is suitable for use in practice, the fermented pulp is pumped to a fibre separator where the alcoholic juice is squeezed out of the pulp. It has been found, for example, that the use of a two-stage roll with a small water wash between the stages can remove about 95% of the ethanol from the fermented pulp. By way of comparison, the same treatment applied to raw pulp prior to fermentation has been found to remove only about 65% of the sugar from the raw pulp.

As noted above, the alcoholic juice obtained by squeezing of the fermented pulp is found to contain almost all of the yeast, together with some fine fibres. Both the yeast and the fibres can be recovered by centrifuging the juice, and the yeast thereby recovered may be recycled to the fermenter, together with some fresh yeast. The liquor obtained after centrifuging the alcoholic juice may be distilled in a fractionation column to obtain the 95% ethanol azeotrope in the usual way. Since very little, if any, water has been added throughout the process of the present invention, and the liquor distilled in the fractionation column is free of suspended solids due to the prior contrifuging step, the volume and BOD of the waste liquor or "slops" from the distillation column are relatively low, hence reducing effluent and environmental problems.

The attached block diagram schematically illustrates by way of example, the steps of a process in accordance with the present invention. The process is further illustrated by the following Examples.

EXAMPLE 1

Effect of Particle Size and Yeast Concentration

Sugar beet was pulped in a Bauer defibrator to two particle sizes, one about 3 mm diameter (referred to as "coarse" pulp) and another about 0.5 mm diameter (referred to as "fine" pulp). The dry matter content was found to be 28.9% in the coarse pulp and 30.8% in the fine pulp. Both were acidified with a little dilute sulphuric acid to lower the pH from the usual value of 6.4 to about 4.5, the optimum value for the alcohol fermentation. No nutrients or enzymes were added in this experiment.

50 gm samples of the coarse (17.0% sucrose) and fine (18.9% sucrose) pulp were weighed into 250 ml Erlenmeyer flasks and various volumes of yeast suspension (active dry baker's yeast or compressed yeast made up to 40 gm/liter in distilled water) were mixed thoroughly with each sample so as to give final yeast concentrations of 3,6 and 9 gm/liter. The flasks were then fitted with a stopper and gas release valve, weighed and incubated at 30° C. for a total of 29 hours, the flasks being weighed at intervals to check the loss of weight due to the escape of carbon dioxide produced by the fermentation.

The results showed that the fermentation was completed in 38 hours with 3 gm/liter yeast, 24 hours with 6 gm/liter and 16 hours with 9 gm/liter. The use of dry or compressed yeast made no noticeable difference to the rate of the fermentation but a more dilute yeast suspension does make it easier to mix thoroughly with the pulp. The water contained in the yeast suspension is readily soaked up by the pulp, so there is no change in its consistency or any evidence of free liquid separating during the fermentation.

The fermented pulps were distilled under vacuum and the ethanol contents measured by gas chromatography. It was found that with a yeast concentration of 6 gm/liter, the yield of alcohol was 4.2 gm per sample (91–92% of the theoretical yield) with the coarse pulp and 4.0–4.3 gm (79–85%) with the fine pulp. Some variability in the results was experienced due to small size of the samples tested, but the coarse pulp was clearly no worse than the fine pulp, despite the lack of fluidity and mixing of the pulp solids after the start of the fermentation.

EXAMPLE 2

1 kg of coarse sugar beet pulp was acidified with dilute sulphuric acid to lower the pH to 4.5. Again, no nutrients or enzymes were added. Then 9 gm (dry weight) yeast in 100 ml water was added to 955 gm pulp (22.59% solids, 8.92% sucrose) and mixed well, the water being soaked up by the pulp to leave substantially no free liquid in the mixture. The mixture was allowed to ferment in a 2 liter Erlenmeyer flask fitted with a water condenser and the volume of carbon dioxide evolved was measured with a wet test gas meter (35.1 liters measured). As a check on the gas volumes, the loss of weight of the flask contents was measured periodically over a period of 20 hours. Of an initial weight of 1094.1 gm, 72.4 gm was lost during the fermentation, leaving 1021.7 gm fermented pulp. A 50.8 gm sample was taken to check the alcohol content by distillation and a 933.4 gm sample was pressed in a rubber-covered steel rolls under heavy pressure so as to squeeze out the alcoholic juice. Of this later sample, 451.4 gm was collected as juice and 448.7 gm as fibre. Then 157.9 gm water was sprinkled onto the pressed fibre and it was pressed again to recover some more liquor. This time, 168.0 gm liquor and 417.4 gm fibre were collected. Due to the small scale of this experiment, there was an unavoidable loss of some material (about 3.5% in each pressing). The liquors from each pressing were analysed and found to contain 27.0 gm ethanol, 0.125 gm yeast and 0.017 gm fibre (fine particles only) in the first liquor and 5.9 gm ethanol, 0.075 gm yeast and 0.010 gm fibre in the second liquor. Overall, this represented a 95% recovery of alcohol and 85% recovery of yeast from the fermented pulp in the two pressings. An additional pressing increases the yeast recovery to 95%.

EXAMPLE 3

Stems of fresh sweet sorghum were cut into small pieces about 1 cm long and milled to produce a coarse pulp. The pulp was acidified with dilute sulphuric acid to lower the pH to 4.5 and no nutrients or enzymes were added. Then 9 gm (dry weight) yeast in 90 ml water was added to 1000 gm of the acidified pulp (22.97% solids, 7.99% sucrose) and mixed well, the water being soaked up by the pulp to leave substantially no free liquid in the mixture. The mixture was allowed to ferment in a 2 liter flask fitted with a water condenser and a dry-ice trap. The volume of carbon dioxide evolved was measured with a wet test gas meter (16.29 liters measured). As a check on the gas volumes, the loss of weight of the flask contents was measured periodically over a period of 24 hours. Of an initial weight of 1093.6 gm, 47.3 gm was lost during the fermentation, leaving 1046.3 gm fermented pulp. Small samples were taken to check the sucrose (0.09% measured), ethanol (3.68% w/w measured) and dry matter (13.47% measured), and a 700 gm sample was pressed in a rubber-covered steel roll under heavy pressure so as to squeeze out the alcoholic juice. Of this larger sample 486.6 gm was collected as juice and 190.1 gm as fibre. Then 140.0 gm water was sprinkled onto the presssed fibre and it was pressed again to recover some more liquor (141.7 gm). The liquors from both pressings were analysed and found to contain 22.4 gm ethanol in the first liquor and 2.3 gm ethanol in the second liquor. Overall, this represented a 95.7% recovery of ethanol in the two pressings.

Ethanol (as the 95% azeotrope) and a yeast/fine fibre mixture are recovered from the liquors by centrifugation and distillation as described above.

In general the process of the present invention is found to provide an unexpectedly rapid and efficient fermentation of a sugar-containing material in the "solid phase" (i.e. in the absence of any substantial amounts of free liquid), together with a highly efficient removal of the ethanol and yeast from the pulp after fermentation. These factors enable much more economic production of fuel ethanol, such that the process becomes economical on a much smaller scale than is the case with the existing technology. Moreover, since most of the equipment required to carry out the process is fairly small and simple, it can be constructed in a modest engineering workshop and would be inherently less expensive than the equipment required in the known ethanol production processes.

Turning now to the use of starch-containing raw material it has been found that instead of cooking the starch crops to make a mash as is usual practice in all breweries and distilleries, immobilised enzymes and yeast may be added to the raw milled crop material, thus allowing the ethanol fermentation to proceed simultaneously with the hydrolysis of the starch at a low temperature (e.g. 25°–50° C.). Amylase used in conjunction with the conversion of starch-containing materials requires a similar pH to that required for the yeast fermentation. The pH may be adjusted by adding either alkali or acid to establish the optimum pH value. The alcoholic liquor may then be squeezed from the residual solids, and the immobilised enzymes and yeast may be recycled. Ethanol is recovered in the normal way be distillation of the alcoholic liquor.

The immobilization of the enzymes on small solid particles in order that they can be recovered together with the yeast provides an additional advantage wherein no substantial modification is necessary to the process or apparatus in relation to sugar crops. In particular, no vacuum distillation is required.

The following example illustrates the conversion of starch-containing materials to ethanol.

EXAMPLE 4

To 49.87 gm raw milled cassava, 0.2% w/w each of three enzymes (a cellulase, a fungal amylase and an amyloglucosidase) and 0.9% w/w (dry matter) baker's yeast were added and mixed well in a small flask. A condenser was fitted to the flask and the flask was incubated in a water bath at 30° C. The weight of the flask was checked at intervals in order to determine the amount of carbon dioxide produced. After incubation for 19 hours, 3.52 gm had been lost and since the cassava contained 28% starch, the weight loss corresponded to a fermentation yield of 46.3%. Owing to the small scale of this experiment, the residue was not pressed.

It is to be noted that the actual alcohol concentration was not determined in this particular example. Larger experiments are to be conducted after conditions have been optimised, which include the use of special enzymes which are more potent with raw starch substrate. However, this experiment illustrates that the simultaneous hydrolysis and fermentation of raw starch can occur in a reasonable time to a low temperature, such as 30° C.

The described arrangement has been advanced merely by way of explanation and many modifications may be made thereto without departing from the spirit and scope of the invention as defined in and appended claims.

We claim:

1. A process for the production of ethanol by solid phase fermentation of solid moist particles of a carbohydrate-containing material, comprising
   (a) crushing or pulping said carbohydrate-containing material to produce, as the sole source of pulp, a pulp containing substantially no free liquid and comprising particles of said material having diameters of the range up to about 10 mm;
   (b) converting non-sugar carbohydrates, if present in said material, to sugars;
   (c) mixing a suspension of yeast with said pulp, the liquid portion of the suspension being absorbed by the pulp so as to leave substantially no free liquid in the mixture and fermenting said mixture by maintaining said mixture under fermentation conditions, to allow said yeast to convert sugars in said pulp to ethanol wherein said pulp during fermentation is relatively stiff in consistency and does not flow of its own accord, yet is pumpable; and
   (d) extracting ethanol from said fermented pulp.

2. A process for the production of ethanol by solid phase fermentation of solid moist particles of a sugar-containing material comprising
   (a) crushing or pulping said sugar-containing material, as the sole source of pulp, to produce a pulp containing substantially no free liquid and comprising particles of said material having diameters up to about 10 mm;
   (b) mixing a suspension of yeast with said pulp, the liquid portion of the suspension being absorbed by the pulp so as to leave substantially no free liquid in the mixture;
   (c) fermenting said mixture by maintaining said mixture under fermentation conditions, to allow said yeast to convert sugar in said particles to alcohol wherein said pulp during fermentation is relatively stiff in consistency and does not flow of its own accord, yet is pumpable; and
   (d) extracting ethanol from said fermented pulp.

3. A process for the production of ethanol by solid phase fermentation of solid moist particles of a starch-containing material, comprising
   (a) crushing or pulping said starch-containing material to produce a pulp containing substantially no free liquid and comprising particles of said material, as the sole source of pulp, having diameters up to about 10 mm;
   (b) saccharifying said pulp to convert starch in said material to sugars;
   (c) simultaneously with or subsequent to said saccharification, mixing a suspension of yeast with said pulp, the liquid portion of the suspension being absorbed by the pulp so as to leave substantially no free liquid in the mixture and fermenting said mixture by maintaining said mixture under fermentation conditions, to allow said yeast to convert sugars in said pulp to ethanol wherein said pulp during fermentation is relatively stiff in consistency and does not flow of its own accord, yet is pumpable; and
   (d) extracting ethanol from said fermented pulp.

4. A process according to any one of claims 1, 2 or 3, wherein the ethanol is extracted from the fermented pulp by pressing or squeezing the pulp to express ethanol containing juice.

5. A process according to claim 4, wherein the extracted juice also contains yeast and fibre from the sugar or starch containing material.

6. A process according to claim 5, wherein yeast and fine fibres are separated from the juice and recycled back to the fermentation step.

7. A process according to claim 6 wherein the separation is achieved by filtration or centrifugation.

8. A process according to any one of claims 1, 2 or 3 in which acid or alkali is added to the pulp to adjust the pH to the range 4 to 6.

9. A process according to claim 2 in which the pH is adjusted to about 4.5.

10. A process according to any one of claims 1, 2 or 3 in which up to about 20% by weight of yeast is added to the pulp.

11. A process according to claim 11 in which about 10 gm dry weight of yeast per kg of wet pulp is added to the pulp.

12. A process according to any one of claims 1, 2 or 3 in which the yeast is high alcohol tolerant.

13. A process according to any one of claims 1, 2 or 3 in which the yeast is thermophilic.

14. A process according to any one of claims 1, 2 or 3 in which the yeast is the strain *Saccharomyces cerevisiae*.

15. A process according to any one of claims 1, 2 or 3 in which the fermentation conditions include a temperature of about 25° C.–50° C.

16. A process according to any one of claims 1 or 2 in which the sugar-containing material is sugar beet, fodder beet, mangolds, sweet sorghum or sugar-cane.

17. A process according to any one of claims 1 or 3 in which the starch-containing material is potatoes, cassava, wheat, barley, triticale, grain sorghum, vegetable waste or corn.

18. A process according to any one of claims 1, 2 or 3 in which an enzyme or mixture of enzymes or growth nutrients for the yeast are added to the mixture.

19. A process according to claim 19 in which the enzyme or mixture of enzymes are immobilized on solid particles or fibres and are recycled following separation of the ethanol containing juice from the fermented pulp.

* * * * *